United States Patent [19]

Miller et al.

[11] 4,241,214

[45] Dec. 23, 1980

[54] METAL SALT COMPLEXES OF 3-ISOTHIAZOLONES

[75] Inventors: George A. Miller, Glenside; Ernest D. Weiler, Fort Washington, both of Pa.

[73] Assignee: Rohm and Haas Company, Philadelphia, Pa.

[21] Appl. No.: 923,845

[22] Filed: Jul. 12, 1978

Related U.S. Application Data

[62] Division of Ser. No. 142,775, May 12, 1971, Pat. No. 4,150,026.

[51] Int. Cl.$^3$ ............................ C07F 1/08; C07F 3/00; C07F 15/00
[52] U.S. Cl. .................................. 548/101; 548/108; 548/109

[58] Field of Search ............... 260/299, 302 A, 304 A, 260/306.7 R, 306.7 E; 424/245, 270, 209, 213; 548/108, 101

[56] References Cited

U.S. PATENT DOCUMENTS

| | | | |
|---|---|---|---|
| 3,523,121 | 8/1970 | Lewis et al. | 260/302 A |
| 3,544,580 | 12/1970 | Lewis et al. | 260/299 |
| 3,562,283 | 2/1971 | Lewis et al. | 260/302 A |
| 3,647,810 | 3/1972 | Bayer et al. | 260/299 |
| 3,801,575 | 4/1974 | Lewis et al. | 260/299 X |
| 4,067,878 | 1/1978 | Miller et al. | 260/302 A |

Primary Examiner—Donald G. Daus
Assistant Examiner—Diana G. Rivers
Attorney, Agent, or Firm—Robert A. Doherty

[57] ABSTRACT

Metal salt complexes of 3-isothiazolones and compositions containing them exhibit useful biocidal properties, including bactericidal, fungicidal, and algaecidal properties.

10 Claims, No Drawings

METAL SALT COMPLEXES OF 3-ISOTHIAZOLONES

This is a division of application Ser. No. 142,775 filed May 12, 1971, now U.S. Pat. No. 4,150,056, and is related to a companion divisional application, Ser. No. 928,205, filed July 12, 1978.

This invention relates to novel metal salt complexes of 3-isothiazolones, their preparation, biocidal compositions containing them, and their use in the control of living organisms.

The novel metal salt complexes of the invention are represented by the formula

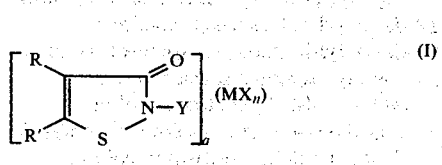

wherein
- Y is a substituted alkyl group of 1 to 18 carbon atoms, an unsubstituted or halogen substituted alkenyl or alkynyl group of 2 to 18 carbon atoms, and preferably 2 to 4 carbon atoms, an unsubstituted or substituted cycloalkyl group of 3 to 12 carbon atoms, preferably having a 3 to 8 carbon atom ring, an unsubstituted or substituted aralkyl group of up to 10 carbon atoms, or an unsubstituted or substituted aryl group of up to 10 carbon atoms;
- R is hydrogen, halogen, or a ($C_1$–$C_4$)alkyl group;
- R' is hydrogen, halogen, or a ($C_1$–$C_4$)alkyl group; or
- R and R' can be taken together to complete a benzene ring, optionally substituted with one or more halogen atoms, nitro groups, ($C_1$–$C_4$)alkyl groups, cyano groups, ($C_1$–$C_4$)alkoxy groups, or the like;
- M is a cation of a metal, such as barium, cadmium, calcium, chromium, cobalt, copper, iron, lead, lithium, manganese, mercury, nickel, sodium, silver, strontium, tin, zinc, or the like;
- X is an anion forming a compound with the cation M, in which the compound has sufficient solubility to form a complex of the invention;
- a is the integer 1 or 2; and
- n is an integer which for the anion X satisfies the valence of the cation M.

By a substituted alkyl group is meant an alkyl group having one or more of its hydrogen atoms replaced by another substituent group. Examples of the substituted alkyl groups which characterize the 3-isothiazolones of the metal salt complexes of the invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituted aralkyl groups which characterize the 3-isothiazolones of the metal salt complexes of the invention include halogen-, nitro-, ($C_1$–$C_4$)alkyl-, or ($C_1$–$C_4$)alkoxy-substituted aralkyl groups, and the like.

By a substituted aryl group is meant an aryl group, such as benzene, naphthalene, or pyridine, having one or more of the hydrogen atoms on the aryl ring replaced by another substituent group. Examples of such substituent groups include halogen, cyano, nitro, ($C_1$–$C_4$)alkyl, ($C_1$–$C_4$)alkoxy, ($C_1$–$C_4$)alkylacylamino, ($C_1$–$C_4$)carbalkoxy, sulfamyl, and the like.

Representative Y substituents include cyclopropyl, cyclohexyl, benzyl, 3,4-dichlorobenzyl, 4-methoxybenzyl, 4-chlorobenzyl, 3,4-dichlorophenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, allyl, propynyl, vinyl, carboxyethyl, 1-isothiazolonylethyl, 1,2,2,trichlorovinyl, trimethylcyclohexyl, carboxyethyl, cyclopropyl, cyclopentyl, and the like.

Representative R substituents include hydrogen, bromine, chlorine, iodine, methyl, ethyl, propyl, isopropyl, butyl, t-butyl, and the like.

Representative R' substituents are hydrogen, chlorine, bromine, iodine, methyl, ethyl, propyl, isopropyl, butyl, t-butyl, and the like.

The alkyl substituents represented by Y, R, and R' can have either branched- or straight-chain spatial configuration.

Among the anions which X can represent are chloride, bromide, iodide, sulfate, nitrate, acetate, perchlorate, bisulfate, bicarbonate, oxalate, maleate, p-toluenesulfonate, carbonate, phosphate, and the like. The preferred metals from which M is derived are calcium, copper, magnesium, manganese, nickel, and zinc. Among the metal cations embraced by M are cationic complexes of the metal ions, including complexes with ammonia, simple organic amines, and various heterocyclic organic amines such as pyridines, pyrimidines, and the like.

Typical 3-isothiazolones from which the metal complexes of the invention can be prepared include the following:
- 3-isothiazolone,
- 2-methyl-3-isothiazolone,
- 2-ethyl-3-isothiazolone,
- 2-propyl-3-isothiazolone,
- 2-butyl-3-isothiazolone,
- 2-octyl-3-isothiazolone,
- 2-decyl-3-isothiazolone,
- 2-octadecyl-3-isothiazolone,
- 2-cyclohexyl-3-isothiazolone,
- 4-chloro-2-methyl-3-isothiazolone,
- 4-bromo-2-methyl-3-isothiazolone,
- 5-chloro-2-methyl-3-isothiazolone,
- 5-chloro-2,4-dimethyl-3-isothiazolone,
- 4-bromo-5-chloro-2-methyl-3-isothiazolone,
- 4-bromo-2-cyclohexyl-3-isothiazolone,
- 4,5-dichloro-2-ethyl-3-isothiazolone,
- 4-methyl-2-octyl-3-isothiazolone,
- 4,5-dimethyl-2-octyl-3-isothiazolone,
- 2-benzyl-3-isothiazolone,
- 2-benzyl-4,5-dichloro-3-isothiazolone,
- 2-benzyl-5-chloro-3-isothiazolone,
- 2-(2,4,-dichlorobenzyl)-3-isothiazolone
- 2-(4-methoxybenzyl)-3-isothiazolone
- 2-(4-ethylbenzyl)-3-isothiazolone
- 2-(3,4-dichlorophenyl)-3-isothiazolone,
- 2-(3,4-dichlorophenyl)-4-methyl-3-isothiazolone,
- 2-(2-cyanoethyl)-3-isothiazolone, 2-(2-carbomethoxyethyl)-3-isothiazolone,
2-carbomethoxymethyl-3-isothiazolone,
2-(2-ethoxyethyl)-3-isothiazolone,
2-(3,3,5-trimethylcyclohexyl)-3-isothiazolone,
2-(2-phenoxyethyl)-3-isothiazolone,
2-(2-methoxyethyl)-3-isothiazolone,
2-(3,4-dichloroanilinomethyl)-3-isothiazolone,
2-(4-chloroanilinomethyl)-3-isothiazolone,
2-(4-nitroanilinomethyl)-3-isothiazolone,
2-morpholinomethyl-3-isothiazolone,
2-piperidinomethyl-3-isothiazolone,
2-phenylcarbamoxymethyl-3-isothiazolone,
2-(3-chlorophenylcarbamoxymethyl)-3-isothiazolone,
2-(3,4-dichlorophenylcarbamoxymethyl)-3-isothiazolone,
2-allyl-3-isothiazolone,
2-propynyl-3-isothiazolone,
2-vinyl-3-isothiazolone,
5-chloro-2-vinyl-3-isothiazolone,
2-methoxymethyl-3-isothiazolone,
2-(2-carboxyethyl)-3-isothiazolone,
2-(2-carbobutoxyethyl)-3-isothiazolone,
2-[1-(N-pyrrolidonyl)ethyl]-3-isothiazolone,
2-[1-(N-isothiazolonyl)ethyl]-3-isothiazolone,
2-(1,2,2-trichlorovinyl)-3-isothiazolone,
2-(1-bromo-2-methoxyethyl)-3-isothiazolone,
2-(2-chloroethyl)-3-isothiazolone,
2-(3-chloropropyl)-3-isothiazolone,
2-cyclopropyl-3-isothiazolone,
2-[2-(4-chlorophenyl)ethyl]-3-isothiazolone,
2-hexyl-3-isothiazolone,
2-heptyl-3-isothiazolone,
2-cyclopentyl-3-isothiazolone,
2-(4-chlorophenyl)-3-isothiazolone,
2-(2,4-dichlorophenyl)-3-isothiazolone,
2-(2,3-dichlorophenyl)-3-isothiazolone,
2-(2,5-dichlorophenyl)-3-isothiazolone,
2-(3,4-dichlorophenyl)-3-isothiazolone,
2-(3-chlorophenyl)-3-isothiazolone,
2-phenyl-3-isothiazolone,
2-(2-chlorophenyl)-3-isothiazolone,
2-pentyl-3-isothiazolone,
2-isopropyl-3-isothiazolone,
2-(2-hydroxyethyl)-3-isothiazolone,
2-(2-bromoethyl)-3-isothiazolone,
2-(1,2,2,2-tetrachloroethyl)-3-isothiazolone,
2-chloromethyl-3-isothiazolone,
2-(2-dimethylaminoethyl)-3-isothiazolone,
4,5-dichloro-2-octyl-3-isothiazolone,
4-chloro-2-octyl-3-isothiazolone,
4-bromo-2-octyl-3-isothiazolone,
4-bromo-2-(4-chlorophenyl)-3-isothiazolone,
4-bromo-2-butyl-3-isothiazolone,
2-(2,2,2-trichloro-1-hydroxyethyl)-3-isothiazolone,
2-(2,2,2-tribromo-1-hydroxyethyl)-3-isothiazolone,
2-trichlorobenzyl-3-isothiazolone,
4-methyl-2-isopropyl-3-isothiazolone,
2-(4-methylphenyl)-3-isothiazolone,
2-hydroxymethyl-3-isothiazolone,
2-[2-(N,N-diethylamino-ethyl]-3-isothiazolone,
5-chloro-3-isothiazolone,
4-bromo-3-isothiazolone,
4-bromo-5-chloro-3-isothiazolone,
4-iodo-2-methyl-3-isothiazolone,
5-chloro-2-ethyl-3-isothiazolone,
4-bromo-5-chloro-2-ethyl-3-isothiazolone,
5-chloro-2-propyl-3-isothiazolone,
4-bromo-5-chloro-2-propyl-3-isothiazolone,
5-chloro-2-butyl-3-isothiazolone,
5-chloro-2-hexyl-3-isothiazolone,
5-chloro-2-octyl-3-isothiazolone,
4-bromo-5-chloro-2-octyl-3-isothiazolone,
5-chloro-2-decyl-3-isothiazolone,
5-chloro-2-dodecyl-3-isothiazolone,
5-chloro-2-phenyl-3-isothiazolone,
1,2-benzisothiazolone,
2-ethyl-1,2-benzisothiazolone,
2-butyl-1,2-benisothiazolone,
2-butyl-5-bromo-1,2-benzisothiazolone,
2-pentyl-1,2-benzisothiazolone,
2-hexyl-5-methyl-1,2-benzisothiazolone,
2-t-octyl-1,2-benzisothiazolone,
2-t-octyl-6-ethoxy-1,2-benisothiazolone,
2-nonyl-1,2-benzisothiazolone,
2-dodecyl-1,2-benzisothiazolone,
2-dodecyl-6-methyl-1,2-benzisothiazolone,
2-t-tridecyl-1,2-benzisothiazolone,
2-t-octadecyl-1,2-benzisothiazolone,
2-butyl-4-methyl-1,2-benzisothiazolone,
2-butyl-5-bromo-1,2-benzisothiazolone,
2-pentyl-4,6-dichloro-1,2-benzisothiazolone,
2-pentyl-6-methoxy-1,2-benzisothiazolone,
2-hexyl-5-methyl-1,2-benzisothiazolone,
2-isohexyl-4,5-diethyl-1,2-benzisothiazolone,
2-octyl-4-chloro-1,2-benzisothiazolone,
2-octyl-4,7-dichloro-1,2-benzisothiazolone,
2-t-octyl-6-chloro-1,2-benzisothiazolone,
2-t-octyl-6-ethoxy-1,2-benzisothiazolone,
2-nonyl-4-propoxy-1,2-benzisothiazolone,
2-dodecyl-4,6-dichloro-1,2-benzisothiazolone,
2-dodecyl-6-methyl-1,2-benzisothiazolone,
2-t-tridecyl-6-methyl-1,2-benzisothiazolone,
2-t-octadecyl-4,6-diethyl-1,2-benzisothiazolone,
2-p-n-butylphenyl-1,2-benzisothiazolone,
2-(2,4-dimethylphenyl)-1,2-benzisothiazolone,
2-(2,6-dimethylphenyl)-1,2-benzisothiazolone,
2-p-chlorophenyl-1,2-benzisothiazolone, and the like.

The compounds of this invention are prepared by reacting a 3-isothiazolone of the formula

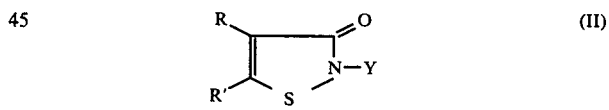

wherein R, R', and Y are as defined above, with a metal salt of the formula $MX_n$, where M, X, and n are as defined above. The following schematic reaction illustrates this preparation:

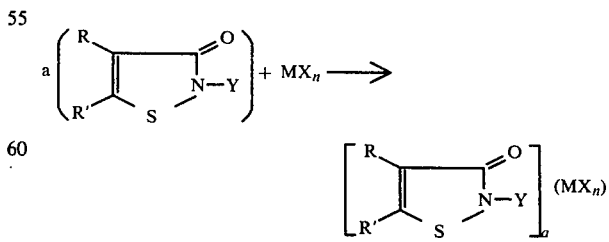

It is preferred that the quantity of reagents used in this reaction correspond to the stoichiometry of the isolated product. However, an excess of the 3-isothiazolone or the metal salt can be used. The complexing of the two reagents generally proceeds readily at room temperature although any temperature in the range of about 0° to 100° C. can be used. The reaction can be run in solution or in a slurry. When the reaction is carried out in solution, the solvent is not critical and can be any in which the two reactants are sufficiently soluble. Preferred are polar solvents such as water and alcohols, such as methanol or ethanol. The resulting 3-isothiazolone metal salt complex may precipitate or may remain in solution. When the product is an insoluble solid it can be isolated by filtration; otherwise, the product can be isolated by removal of the solvent.

Some of the halide metal salt complexes of the invention can be prepared by reacting a hydrohalide salt, such as a hydrochloride salt or a hydrobromide salt, of a 3-isothiazolone with a metal oxide, such as for example zinc oxide, calcium oxide, or magnesium oxide. The following schematic reaction illustrates this preparation

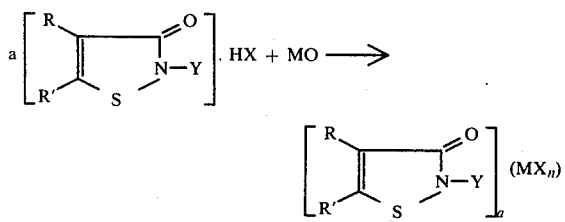

Procedures similar to those described above are also applicable to this reaction.

The metal salts used in preparing the metal salt complexes of the invention are soluble salts or become sufficiently soluble during the reaction that a complex of the invention will be formed.

The 3-isothiazolone metal salt complexes are solids with characteristic melting or decomposition points. In many instances they may be recrystallized from appropriate solvents such as water, ethanol, methanol, diethylether, benzene, toluene, methylene chloride, dimethylformamide, chloroform, acetone, methylethylketone, and the like, or mixtures of such solvents.

The preparation and properties of the 3-isothiazolones from which metal salt complexes of the invention can be made are described in U.S. patent applications Ser. No. 836,660, now U.S. Pat. No. 3,761,488, granted Sept. 25, 1973, Ser. No. 855,046 filed Sept. 3, 1969, now abandoned, by S. N. Lewis, G. A. Miller, and A. B. Law, and Ser. No. 841,548 filed July 14, 1969 by S. N. Lewis and G. A. Miller, now U.S. Pat. No. 3,849,430, granted Nov. 19, 1974.

The benzisothiazolones from which metal salt complexes of Formula I can be made are prepared by the reaction of a primary amine with an o-halosulfenylbenzoyl halide or the intramolecular condensation of an o-halosulfenylbenzamide. The method of preparation of these benzisothiazolones is described in U.S. Pat. No. 3,517,022, of Miller et al., granted on June 23, 1970.

The following examples are set forth to illustrate further this invention but are not intended to limit it in any way. In Table I, typical metal salt complexes of the invention prepared by the above-described processes and constituting Examples 1 to 55 are listed. Table II sets forth the elemental analyses and melting ranges of the complexes listed in Table I. Specific illustrative preparations of the complexes of Examples 1, 13, 17, 19, 23, 53, 54 and 56 are described after Tables I and II.

TABLE I

METAL SALT COMPLEXES OF 3-ISOTHIAZOLONES

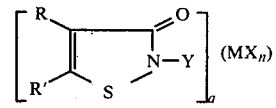

| Example No. | Y | R' | R | a | M | X | n | Yield (%) |
|---|---|---|---|---|---|---|---|---|
| 1 | CH$_3$ | H | H | 2 | Zn | Cl | 2 | 92 |
| 2 | CH$_3$ | H | H | 2 | Zn | SO$_4$ | 1 | 71 |
| 3 | CH$_3$ | H | H | 1 | Cu | Cl | 2 | 47 |
| 4 | CH$_3$ | Cl | H | 2 | Zn | Cl | 2 | 95 |
| 5 | CH$_3$ | Cl | H | 2 | Zn | Br | 2 | 80 |
| 6 | CH$_3$ | Cl | H | 2 | Zn | I | 2 | 42 |
| 7 | CH$_3$ | Cl | H | 2 | Zn | OAc | 2 | 81 |
| 8 | CH$_3$ | Cl | H | 1 | Zn | SO$_4$ | 1 | 65 |
| 9 | CH$_3$ | Cl | H | 2 | Zn | NO$_3$ | 1 | — |
| 10 | CH$_3$ | Cl | H | 1 | Cu | Cl | 2 | 82 |
| 11 | CH$_3$ | Cl | H | 1 | Cu | Br | 2 | 95 |
| 12 | CH$_3$ | Cl | H | 2 | Ni | Cl | 2 | 87 |
| 13 | CH$_3$ | Cl | H | 2 | Mn | Cl | 2 | 89 |
| 14 | CH$_3$ | Cl | H | 1 | Ca | Cl | 2 | 87 |
| 15 | CH$_3$ | Cl | H | 1 | Mg | Cl | 2 | 31 |
| 16 | CH$_3$ | Cl | H | 1 | Hg | Cl | 2 | 92 |
| 17 | CH$_3$ | Cl | H | 1 | Cd | Cl | 2 | 100 |
| 18 | C$_4$H$_9$-n | H | H | 2 | Zn | Cl | 2 | 93 |
| 19 | C$_4$H$_9$-t | H | H | 2 | Zn | Cl | 2 | 91 |
| 20 | C$_6$H$_{13}$-n | H | H | 2 | Zn | Cl | 2 | 87 |
| 21 | C$_8$H$_{17}$-n | H | H | 2 | Zn | Cl | 2 | 88 |
| 22 | C$_8$H$_{17}$-n | H | H | 2 | Zn | Br | 2 | 75 |
| 23 | C$_8$H$_{17}$-n | H | H | 2 | Cu | Cl | 2 | 74 |
| 24 | C$_8$H$_{17}$-n | H | H | 1 | Cd | Cl | 2 | 75 |
| 25 | C$_8$H$_{17}$-n | H | H | 2 | Sn | Cl | 2 | — |
| 26 | C$_8$H$_{17}$-n | H | H | 2 | Co | Cl | 2 | 79 |
| 27 | C$_3$H$_{17}$-n | H | H | 2 | Fe | Cl | 3 | — |
| 28 | C$_{10}$H$_{21}$-n | H | H | 2 | Zn | Cl | 2 | 90 |
| 29 | H | H | H | 2 | Zn | Br | 2 | 74 |
| 30 | H | H | H | 2 | Cu | Cl | 2 | 73 |
| 31 | CH$_3$ | H | H | 2 | Ca | Cl | 2 | 86 |

TABLE I-continued
METAL SALT COMPLEXES OF 3-ISOTHIAZOLONES

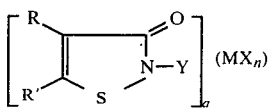 (MX$_n$)$_a$

| Example No. | Y | R' | R | a | M | X | n | Yield (%) |
|---|---|---|---|---|---|---|---|---|
| 32 | CH$_3$ | Cl | H | 2 | Co | Cl | 2 | 71 |
| 33 | CH$_3$ | H | H | 2 | Mg | Cl | 2 | 95 |
| 34 | CH$_3$ | H | H | 1 | Ca | Cl | 2 | 93 |
| 35 | CH$_3$ | H | H | 2 | Mn | Cl | 2 | 88 |
| 36 | C$_4$H$_9$-n | H | H | 1 | Ca | Cl | 2 | 99 |
| 37 | C$_4$H$_9$-sec | H | CH$_3$ | 2 | Zn | Cl | 2 | 75 |
| 38 | C$_4$H$_9$-sec | H | CH$_3$ | 2 | Zn | Br | 2 | 65 |
| 39 | C$_6$H$_{13}$-n | H | H | 1 | Ca | Cl | 2 | 95 |
| 40 | CH$_2$CH(C$_2$H$_5$)C$_4$H$_9$-n | H | H | 2 | Zn | Cl | 2 | 63 |
| 41 | C$_8$H$_{17}$-n | H | H | 1 | Ca | Cl | 2 | 64 |
| 42 | C$_8$H$_{17}$-n | H | H | 2 | Cr | Cl | 2 | 93 |
| 43 | C$_8$H$_{17}$-n | H | H | 1 | Ni | Cl | 2 | 72 |
| 44 | C$_8$H$_{17}$-n | H | H | 1 | Fe | Cl | 2 | — |
| 45 | C$_H{17}$-n | H | H | 1 | Mn | Cl | 2 | 46 |
| 46 | C$_9$H$_{19}$-n | H | H | 2 | Zn | Cl | 2 | 79 |
| 47 | C$_6$H$_5$ | H | H | 2 | Zn | Cl | 2 | 93 |
| 48 | C$_6$H$_4$Cl(3) | H | H | 2 | Zn | Cl | 2 | 90 |
| 49 | C$_6$H$_4$Cl(3) | H | H | 2 | Zn | Br | 2 | 84 |
| 50 | CH$_2$C$_6$H$_4$CH$_3$(4) | H | H | 2 | Zn | Cl | 2 | 98 |
| 51 | C$_2$H$_4$C$_6$H$_4$Cl(4) | H | H | 2 | Zn | Cl | 2 | 96 |
| 52 | H | H | H | 2 | Zn | Cl | 2 | 76 |
| 53 | H | —C$_4$H$_4$— | | 2 | Zn | Cl | 2 | 73 |
| 54 | H | —C$_4$H$_4$— | | 2 | Mn | Cl | 2 | 77 |
| 55 | H | —C$_4$H$_4$— | | 2 | Cu | Cl | 2 | 46 |
| 56 | CH$_3$ | Cl | H | 2 | Ca | Cl | 2 | 60 |

TABLE II
ELEMENTAL ANALYSIS

| Example No. | mp °C. | Empirical Formula | C | H | N | S | X | M |
|---|---|---|---|---|---|---|---|---|
| 1 | 148–151 | C$_4$H$_5$NOS ½ ZnCl$_2$ | 26.18(26.21) | 3.00(2.75) | 7.57(7.62) | 17.46(17.49) | 19.31(19.31) | 17.90(17.83) |
| 2 | >250 | C$_4$H$_5$NOS ½ ZnSO$_4$ | 20.79(19.80) | 2.76(2.06) | 6.01(5.77) | 21.34(19.85) | | 18.85(13.45) |
| 3 | 215–220 | C$_4$H$_5$NOS CuCl$_2$ | 19.35(19.17) | 2.21(21.41) | 5.46(5.58) | 10.96(12.79) | 29.17(28.30) | 24.86(25.35) |
| 4 | 109–112 | C$_4$H$_4$ClNOS ½ZnCl$_2$ | 22.13(22.07) | 1.96(1.85) | 6.43(6.43) | 14.42(14.72) | 32.31(32.57) | 15.40(15.01) |
| 5 | 126–129 | C$_4$H$_4$ClNOS ½ ZnBr$_2$ | 18.72(18.32) | 1.58(1.53) | 5.51(5.34) | 12.68(12.21) | Br: 27.83(30.53) Cl: 13.48(13.55) | 12.46(12.40) |
| 6 | 115–118 | C$_4$H$_4$ClNOS ½ ZnI$_2$ | 15.69(15.53) | 1.49(1.29) | 4.43(4.53) | 11.35(10.36) | 11.23(11.49) | 10.44(10.52) |
| 7 | 129–135 | C$_4$H$_4$ClNOS ½ Zn(OCOCH$_3$)$_2$ | 29.03(29.88) | 2.59(2.90) | 5.42(5.81) | 12.33(13.28) | 12.35(14.73) | 15.12(13.48) |
| 8 | — | C$_4$H$_4$ClNOS ZnSO$_4$ 2H$_2$O | 11.00(13.85) | 2.10(2.31) | 3.04(4.04) | 18.51(18.47) | 7.04(10.25) | 23.01(18.76) |
| 9 | — | C$_4$H$_4$ClNOS ½ Zn(NO$_3$)$_2$ | 19.59(19.67) | 1.96(1.64) | 10.90(11.48) | 13.09(13.11) | 13.95(14.55) | 13.17(13.32) |
| 10 | 195–200 | C$_4$H$_4$ClNOS CuCl$_2$ | 17.62(16.90) | 1.56(1.41) | 5.11(4.93) | 11.51(11.27) | 33.59(37.50) | 19.78(22.36) |
| 11 | 143–145 | C$_4$H$_4$ClNOS CuBr$_2$ | 13.75(12.87) | 1.46(1.07) | 3.82(3.75) | 7.64(8.58) | 9.49(9.52) | 17.15(17.02) |
| 12 | >250 | C$_4$H$_4$ClNOS ½ NiCl$_2$ | 21.84(22.38) | 2.07(1.86) | 6.19(6.53) | (14.94) | 31.32(33.10) | 13.93(13.75) |
| 13 | >250 | C$_4$H$_4$ClNOS ½ MnCl$_2$ | 22.46(22.59) | 1.84(1.88) | 6.41(6.59) | 15.35(15.06) | 33.45(33.41) | 13.58(12.94) |
| 14 | >250 | C$_4$H$_4$ClNOS CaCl$_2$ ½ H$_2$O | 19.89(17.81) | 2.03(1.86) | 5.63(5.19) | 11.90(11.87) | 32.15(39.52) | 10.64(14.84) |
| 15 | 132–136 | C$_4$H$_4$ClNOS MgCl$_2$ | 21.04(20.60) | 3.55(3.05) | 6.01(6.01) | 14.06(13.73) | 28.53(30.47) | |
| 16 | 122 | C$_4$H$_4$ClNOS HgCl$_2$ | 11.50(11.40) | 1.06(0.95) | 3.13(3.33) | 7.76(7.60) | 18.39(25.30) | 47.50(47.62) |
| 17 | >250 | C$_4$H$_4$ClNOS CiCl$_2$ | 14.53(14.44) | 1.41(1.20) | 3.98(4.21) | 9.49(9.62) | 31.92(32.03) | 35.19(36.00) |
| 18 | 66–67 | C$_7$H$_{11}$NOS ½ ZnCl$_2$ | 36.96(37.30) | 4.97(4.92) | 6.22(6.21) | 14.06(14.23) | 15.91(15.73) | 14.38(14.50) |
| 19 | 130–132 | C$_7$H$_{11}$NOS ½ ZnCl$_2$ | 37.06(37.30) | 4.92(4.92) | 6.19(6.21) | 14.43(14.23) | 15.64(15.73) | 14.34(14.50) |
| 20 | 52–54 | C$_9$H$_{15}$NOS ½ ZnCl$_2$ | 42.53(42.66) | 5.90(5.97) | 5.48(5.52) | 12.44(12.65) | 13.31(13.99) | 13.01(12.90) |
| 21 | 63–64 | C$_{11}$H$_{19}$NOS ½ ZnCl | 47.11(46.94) | 7.14(7.27) | 4.99(4.97) | 11.50(11.39) | 12.60(12.60) | 11.63(11.61) |
| 22 | 61–63 | C$_{11}$H$_{19}$NOS ½ ZnBr$_2$ | 40.34(40.54) | 5.71(5.87) | 4.30(4.29) | 9.62(9.84) | 24.47(24.51) | 9.63(10.02) |
| 23 | 63–65 | C$_{11}$H$_{19}$NOS ½ CuCl$_2$ | 46.93(47.04) | 6.93(6.82) | 4.92(4.99) | 11.51(11.43) | 13.33(12.64) | 11.45(11.32) |
| 24 | >250 | C$_{11}$H$_{19}$NOS ½ ClCl$_2$ | 33.90(33.31) | 4.83(4.83) | 3.52(3.53) | 8.19(8.08) | 18.19(17.88) | 29.73(28.34) |
| 25 | oil | C$_{11}$H$_{19}$NOS ½ SnCl$_2$ H$_2$O | 42.34(41.80) | 6.24(6.08) | 4.29(4.43) | 10.02(10.14) | 10.16(10.14) | 18.53(17.80) |
| 26 | 74–75 | C$_{11}$H$_{19}$NOS ½ CoCl$_2$ H$_2$O | 44.61(44.60) | 6.78(6.46) | 4.72(4.72) | 9.47(10.08) | 14.50(12.00) | 11.53(8.93) |
| 27 | oil | C$_{11}$H$_{19}$NOS ½ FeCl$_3$ | 46.16(44.87) | 6.20(6.50) | 4.50(4.75) | 9.96(10.89) | 17.51(18.05) | 9.15(9.48) |
| 28 | 65–67 | C$_{13}$H$_{23}$NOS ½ ZnCl$_2$ | 50.85(50.45) | 7.57(7.49) | 4.52(4.52) | 10.02(10.36) | 11.66(11.45) | 10.64(10.56) |
| 29 | 163–165 | C$_3$H$_3$NOS ½ ZnBr$_2$ | 17.17(16.86) | 1.38(1.41) | 6.43(6.55) | 15.15(15.00) | 37.26(37.39) | 15.14(15.29) |
| 30 | 190–193 | C$_3$H$_3$NOS ½ CuCl$_2$ | 21.55(21.40) | 1.90(1.80) | 8.12(8.31) | 18.70(19.04) | 20.87(21.06) | 18.31(18.87) |
| 31 | >250 | C$_4$H$_5$NOS ½ CaCl$_2$ ¼ H$_2$O | 27.40(28.15) | 3.21(2.93) | 7.93(8.21) | 17.24(18.77) | 18.83(20.82) | 11.08(11.73) |
| 32 | >250 | C$_4$H$_4$ClNOS C$_6$Cl$_2$H$_2$O | 18.17(16.13) | 2.06(2.02) | 5.09(4.71) | 9.88(10.76) | 35.46(35.80) | 20.08(19.83) |
| 33 | 114–117 | C$_4$H$_5$NOS ½ MgCl$_2$ 2H$_2$O | 24.68(24.18) | 4.82(4.52) | 6.38(7.05) | 15.72(16.12) | 16.93(17.88) | 12.08(15.15) |
| 34 | >250 | C$_4$H$_5$NOS CaCl$_2$3/2H$_2$O | 19.30(18.97) | 3.52(3.16) | 5.26(5.53) | 12.97(12.65) | 23.72(28.06) | 10.87(15.81) |
| 35 | 238(dec) | C$_4$H$_5$NOS ½ MnCl$_2$ | 26.87(26.97) | 2.97(2.81) | 7.68(7.86) | 18.06(17.98) | 20.30(19.94) | 15.15(15.45) |
| 36 | >250 | C$_7$H$_{11}$NOS CaCl$_2$ | 32.21(31.34) | 4.06(4.10) | 4.90(5.22) | 10.13(11.94) | 24.91(26.49) | |
| 37 | 92-93 | C$_8$H$_{13}$NOS ½ ZnCl$_2$ | 40.30(40.13) | 5.76(5.47) | 5.78(5.85) | 13.22(13.39) | 15.03(14.81) | 13.71(13.65) |

TABLE II-continued

ELEMENTAL ANALYSIS

| Example No. | mp °C | Empirical Formula | C | H | N | S | X | M |
|---|---|---|---|---|---|---|---|---|
| 38 | 124–126 | C$_8$H$_{13}$NOS ½ ZnBr$_2$ | 34.05(33.85) | 4.58(4.62) | 4.82(4.92) | 11.38(11.28) | 28.16(28.15) | 11.23(11.51) |
| 39 | >250 | C$_9$H$_{15}$NOS . CaCl$_2$ | 36.03(36.49) | 5.25(5.07) | 4.53(4.73) | 9.13(10.81) | 24.29(23.99) | |
| 40 | 73–76 | C$_{11}$H$_{19}$NOS ½ ZnCl$_2$ | 46.70(46.98) | 6.54(6.76) | 4.96(4.98) | 10.99(11.39) | 13.26(12.63) | |
| 41 | 251(dec) | C$_{11}$H$_{19}$NOS CaCl$_2$4H$_2$O | 33.57(33.33) | 6.25(6.82) | 3.87(3.53) | 8.01(8.08) | 23.72(28.06) | 11.55(10.10) |
| 42 | 113–123 | C$_{11}$H$_{19}$NOS CrCl$_2$ . 2H$_2$O | 36.28(35.48) | 6.87(6.18) | 3.24(3.76) | 7.17(8.60) | 18.27(19.09) | |
| 43 | >250 | C$_{11}$H$_{19}$NOS . NiCl$_2$ | 39.03(38.48) | 5.81(5.54) | 4.02(4.08) | 6.66(9.33) | 17.93(20.70) | |
| 44 | | C$_{11}$H$_{19}$NOS . FeCl$_2$ | 36.65(38.82) | 5.61(5.59) | 3.79(4.12) | 7.87(9.41) | 20.80(20.88) | |
| 45 | >250 | C$_{11}$H$_{19}$NOS . MnCl$_2$ . ½ H$_2$O | 35.14(37.93) | 5.63(5.75) | 4.04(4.02) | 8.84(9.19) | 22.86(20.40) | |
| 46 | 60–63 | C$_{12}$H$_{21}$NOS ½ ZnCl$_2$ | 49.01(48.81) | 7.10(7.21) | 4.77(4.75) | 10.81(10.85) | 12.17(12.03) | |
| 47 | 159–162 | C$_9$H$_7$NOS ½ ZnCl$_2$ | 43.86(44.08) | 2.70(2.86) | 5.86(2.86) | 12.88(13.06) | 14.52(14.49) | |
| 48 | 172–175 | C$_9$H$_6$ClNOS ½ ZnCl$_2$ | 38.60(38.63) | 2.11(2.16) | 4.90(5.00) | 11.49(11.45) | 25.02(25.34) | 11.33(11.63) |
| 49 | 150–152 | C$_9$H$_6$ClNOS ½ ZnBr$_2$ | 33.34(33.42) | 1.84(1.86) | 4.15(4.32) | 9.67(9.89) | Br24.56(24.64) Cl10.84(10.94) | |
| 50 | 160–163 | C$_{11}$H$_{11}$NOS . ½ ZnCl$_2$ | 48.43(48.35) | 4.09(4.03) | 5.04(5.13) | 11.56(11.72) | 13.21(13.00) | |
| 51 | 169–171 | C$_{11}$H$_{10}$ClNOS ½ ZnCl$_2$ | 42.65(42.93) | 3.36(3.25) | 4.43(4.55) | 9.97(10.41) | 22.95(23.09) | |
| 52 | 132–136 | C$_3$H$_3$NOS ½ ZnCl$_2$ | 21.50(21.29) | 1.99(1.79) | 8.22(8.27) | 18.64(18.94) | 20.96(20.95) | 19.06(19.31) |
| 53 | 212–214 | C$_7$H$_5$NOS ½ ZnCl$_2$ | 38.12(38.40) | 2.55(2.27) | 6.13(6.40) | | 15.10(16.15) | 14.51(14.75) |
| 54 | >250 | C$_7$H$_5$NOS ½ MnCl$_2$H$_2$O | 37.37(37.67) | 2.40(2.69) | 6.12(6.28) | 14.26(14.35) | 18.27(15.92) | |
| 55 | 250–252 | C$_7$H$_5$NOS ½ CuCl$_2$ | 38.70(38.50) | 2.35(2.31) | 6.21(6.41) | 14.59(14.69) | | |
| 56 | >250 | C$_4$H$_4$ClNOS ½ CaCl$_2$ | 23.38(23.41) | 1.95(2.12) | 6.46(6.83) | 13.21(15.60) | 34.45(34.63) | |

EXAMPLE 1

Preparation of bis-(2-Methyl-3-isothiazolone)-zinc(II)chloride

Method 1

To a solution of 3.4 g (0.02 mole) of anhydrous zinc chloride in 130 ml absolute ethanol was added a solution of 2-methyl-3-isothiazolone in 20 ml of absolute ethanol. The clear solution was stirred at room temperature for 30 minutes. Concentration yielded a tan solid. The solid was triturated with ether, filtered, and dried to yield 8.4 g (92%) of bis-(2-methyl-3-isothiazolone) zinc(II)chloride, m.p. 148°–151° C.

Method 2

A mixture of 7.6 g (0.05 mole) of 2-methyl-3-isothiazolone hydrochloride and 2.2 g (0.025 mole) of zinc oxide were stirred in 100 ml methanol at room temperature for 24 hours. The mixture was filtered in order to remove minute quantities of suspended solid. The filtrate was concentrated to yield 8.5 g (94%) of the metal salt complex.

EXAMPLE 13

Preparation of bis-(5-Chloro-2-methyl-3-isothiazolone)-manganese(II)-chloride To a solution of 3.78 g (0.03 mole) of anhydrous manganese chloride in 100 ml of ethanol was added a solution of 9.0 g (0.06 mole) of 5-chloro-2-methyl-3-isothiazolone in 25 ml of ethanol. The mixture was filtered and the filtrate concentrated to give a pale, pink solid. The solid was triturated with ether, collected and dried to yield 11.4 g (98%) of product, m.p.>250° C.

EXAMPLE 17

Preparation of 5-Chloro-2-methyl-3-isothiazolone-cadmium(II)chloride

To a solution of 5.5 g (0.03 mole) of anhydrous cadmium chloride in 120 ml of ethanol was added a solution of 4.5 g (0.03 mole) of 5-chloro-2-methyl-3-isothiazolone in 25 ml of ethanol. A white precipitate formed immediately. The mixture was filtered and air dried to yield 10.0 g (100%) of product, m.p.>250° C.

EXAMPLE 19

Preparation of bis(2-t-Butyl-3-isothiazolone)-zinc(II)chloride

To a solution of 1.36 g (0.01 mole) of anhydrous zinc chloride in 60 methanol was added a solution of 3.14 g (0.02 mole) of 2-t-butyl-3-isothiazolone in 40 ml methanol. The mixture was stirred at room temperature for 30 minutes. Concentration of the mixture yielded a tan solid. The solid was triturated with ether, filtered, and dried to give 4.1 g (91%) of product, m.p. 130°–132° C.

EXAMPLE 23

Preparation of bis(2-n-Octyl-3-isothiazolone)-copper(II)chloride

To a solution of 3.44 g (0.025 mole) of anhydrous copper chloride in 120 ml absolute ethanol was added a solution of 10.6 g (0.05 mole) of 2-n-octyl-3-isothiazolone in 10 ml absolute ethanol. Concentration of the mixture yielded a dark oil, which slowly crystallized to a light-green solid on standing. The solid was thoroughly washed with ether, filtered and air dried to give 10.4 g (74%) of product, m.p. 65°–67° C.

EXAMPLE 53

Preparation of bis-(1,2-Benzisothiazolin-3-one)zinc(II)chloride

A mixture of 1.5 g (0.01 mol) of 1,2-benzisothiazolin-3-one and 0.68 g (0.005 mol) of anhydrous zinc chloride was stirred in 75 ml methanol at room temperature for ½ hour. The solution was filtered in order to remove traces of suspended solid. The filtrate was concentrated to yield a tan solid. The solid was dried (60°/0.5 mm, 3 hrs.) to afford 1.6 g (73%) of product, m.p. 212°–214° C.

EXAMPLE 54

Preparation of 1,2-Benzisothiazolin-3-one manganese(II)chloride

To a solution of 1.26 g (0.01 mol) of anhydrous manganese chloride was added 4.5 g (0.03 mol) of 1,2-benzisothiazolin in 30 ml of water. The solution was concentrated to give a tan colored solid. The solid was thoroughly washed with dry acetone, filtered and dried at room temperature to yield 3.47 g (77%) of product, m.p. >250° C.

EXAMPLE 56

Preparation of bis(5-chloro-2-methyl-3-isothiazolone)calcium(II)chloride

To a solution of 0.185 g (0.00167 mol) of anhydrous calcium chloride in 10 ml of methanol was added a solution of 0.747 g (0.005 mol) of 5-chloro-2-methyl-3-isothiazolone in 5 ml of methanol. The mixture of solutions was diluted with 200 ml of anhydrous ether. White solid separated and was collected and filtered to give 0.41 g (60%) of product, having a m.p. >250° C.

The novel metal salt complexes of the invention are biocidally active compounds, which are useful for the control of various living organisms and particularly microorganisms. For example, the complexes are especially effective as bactericidal, algaecidal, fungicidal, and slimicidal agents. Furthermore, these novel complexes are resistant to inhibition or decomposition by common additives or contaminants or by extreme conditions.

An advantage of the novel salt complexes of the invention is their greatly increased thermal stability compared to the corresponding 3-isothiazolones. For example, at 50° C., 5-chloro-2-methyl-3-isothiazolone undergoes a 30% decomposition, as determined by gas-liquid chromatography, after 10 days and its hydrochloride slat undergoes a 47 to 58% decomposition after 10 days. However, neither the calcium chloride nor the zinc chloride complex of 5-chloro-2-methyl-3-isothiazolone undergoes any appreciable decomposition after 10 days at 50° C.

Antibacterial and antifungal activity of the complexes of the invention were evaluated by a Serial Dilution Test (Broth Titer Test) in which an organism is added to a series of broths containing two-fold dilutions of a test compound. The values obtained from these tests, which are summarized in Table III, represent the maximum dilution (in parts per million by weight) at which the metal salt complex under evaluation completely controls the test organism. *Staphylococcus aureus* (Staph), *Escherichia coli* (*E. coli*), and *Pseudomonas aeruginosa* (Pseud) were the bacterial organisms employed in this test and the fungi employed were *Aspergillus niger* (*A. niger*) and *Rhizopus stolonifer* (Rhiz). Antialgal activity of the complexes of the invention was determined by a serial dilution modification of the Fitzgerald Test (Applied Microbiology, 7, 205-211(1959). Table III shows the parts per million (by weight) of the metal salt complex under evaluation necessary for complete control of the organism. *Chlorella pyrenoidosa* (Chlor) and "Black" algae (*Phormidium* sp.) were the algae employed in this test.

Metal salt complexes also exhibit insecticidal and postemergence herbicidal activity. Tables IV and V summarize this activity as determined by standard tests.

TABLE III

MICROBIOCIDAL SCREENING DATA
Minimum Inhibitory Concentration, ppm

| Example No. | Bacteria | | | Fungi | | Algae | |
|---|---|---|---|---|---|---|---|
| | Pseud. | Staph | E. coli | A. niger | Rhiz. | Chlor. | "Black" |
| 1 | 63 | 125 | 63 | 500 | 250 | 2.5 | .63 |
| 2 | 63 | 250 | 125 | 500 | 250 | 5 | 1.25 |
| 3 | 31 | 125 | 63 | 500 | 250 | 2.5 | .31 |
| 4 | 4 | 4 | 8 | 8 | 8 | .31 | .16 |
| 5 | 8 | 8 | 8 | 16 | 8 | .31 | .16 |
| 6 | 8 | 8 | 8 | 16 | 8 | .63 | .31 |
| 7 | 8 | 8 | 8 | 16 | 8 | .63 | .31 |
| 8 | 31 | 31 | 31 | 125 | 31 | 1.25 | .63 |
| 9 | 4 | 8 | 8 | — | — | — | — |
| 10 | 8 | 8 | 8 | 16 | 8 | .31 | .16 |
| 11 | 8 | 8 | 8 | 16 | 8 | .31 | .16 |
| 12 | 8 | 8 | 4 | 16 | 8 | .31 | .16 |
| 13 | 4 | 4 | 4 | 8 | 4 | .16 | .16 |
| 14 | 4 | 4 | 4 | 16 | 4 | .31 | .16 |
| 15 | 8 | 4 | 4 | 8 | 4 | .31 | .16 |
| 18 | 500 | 250 | 31 | 63 | 16 | 2.5 | 1.25 |
| 19 | 1000 | 63 | 31 | 63 | 63 | — | — |
| 20 | 1000 | 63 | 125 | 16 | 8 | 5 | 1.25 |
| 21 | 500 | 16 | 125 | 16 | 8 | 5 | 1.25 |
| 23 | 500 | 16 | 125 | 4 | 8 | 2.5 | .63 |
| 24 | 250 | 8 | 125 | 4 | 16 | 5 | .63 |
| 28 | 1000 | 4 | 63 | 16 | 16 | 5 | 1.25 |
| 29 | 63 | 250 | 125 | 63± | 63 | 2.5 | 20 |
| 30 | 31 | 125 | 63 | 125 | 63 | 2.5 | 2.5 |
| 31 | 63 | 125 | 125 | 500± | 125 | 5 | 5 |
| 32 | 4 | 8 | 8 | 8 | 4 | 0.63 | 0.16 |
| 33 | 63 | 125 | 125 | 500± | 250 | 5 | 5 |
| 34 | 125± | 250 | 125 | 500 | 250 | 2.5± | 5 |
| 35 | 63 | 250 | 125 | 500 | 125 | 2.5 | 2.5 |
| 37 | >1000 | >1000 | 1000 | 125 | 125 | 10± | 20 |
| 38 | 1000 | >1000 | 1000 | 125 | 125 | 10± | 20 |
| 41 | 1000 | 31 | 500 | ± at 16 and 8 | 8 | 5± | 5 |
| 46 | 500 | 8 | 63 | 8± | 8 | — | — |
| 47 | 500 | 8 | 63 | 8± | 8 | — | — |
| 48 | 1000 | 8 | 31 | 500± | 500 | 2.5 | 0.63 or < |
| 49 | 1000 | 8 | 63 | 500± | 500 | 2.5 | 0.63 or < |

TABLE IV

INSECTICIDAL ACTIVITY (% KILL AT 1200 PPM)[1]

| Example No. | TSM | TSM(sy) | GPA | BB(F) | AW(F) | HF(Kd) | ME/L | Nema. | Mosq. |
|---|---|---|---|---|---|---|---|---|---|
| 1 | 0 | 0 | 0 | 0(N) | 0(N) | 0(5) | 0/0 | | 0 |
| 2 | 0 | 0 | 0 | 0(N) | 0(N) | 0(0) | 0/0 | | 0 |
| 3 | 0 | 0 | 0 | 0(N) | 0(N) | 0(0) | 0/0 | | 90 |
| 4 | 0 | 0 | 0 | 0(N) | 0 | 25(100) | 0/0 | | 0 |
| 5 | 0 | — | 0 | 0(N) | 0(N) | 15(10) | | | 0 |
| 6 | 0 | — | 0 | 0(N) | 0(N) | 5(0) | | | 0 |
| 7 | 64 | — | 0 | 0(N) | 0(N) | 0(0) | | | 0 |
| 8 | 0 | 0 | 0 | 0(N) | 0(N) | 0(0) | 0/0 | | 0 |
| 9 | 67 | — | 0 | 0(N) | 0(N) | 10(5) | | | 0 |
| 11 | 0 | 0 | 0 | 0(N) | 0(N) | 5(0) | 99/0 | | 80 |
| 12 | 0 | — | 38 | 0(N) | 0(N) | 0(10) | | | 0 |
| 13 | 76 | — | 0 | 0(N) | 0(N) | 20(20) | | | 0 |
| 14 | 0 | 0 | 0 | 0(N) | 0(N) | 30(0) | 0/0 | 0 | 0 |
| 15 | 57 | — | 0 | 0(N) | 0(N) | 25(0) | | | 0 |
| 16 | 75m | 0 | 43 | 0(N) | 0(N) | 60(20) | 85/0 | | 0 |
| 17 | 0 | — | 0 | 0(N) | 0(N) | 0(5) | | | 0 |

TABLE IV-continued

INSECTICIDAL ACTIVITY (% KILL AT 1200 PPM)[1]

| Example No. | TSM | TSM(sy) | GPA | BB(F) | AW(F) | HF(Kd) | ME/L | Nema. | Mosq. |
|---|---|---|---|---|---|---|---|---|---|
| 18 | 0 | 0 | 0 | 0(N) | 0(N) | 0(0) | 0/0 | | |
| 19 | 0 | 0 | 0 | 0(N) | 0(N) | 5(0) | 0/0 | | 0 |
| 20 | 0 | 0 | 0 | 0(N) | 0(N) | 5(0) | 0/0 | | 0 |
| 21 | 93 | 0 | 41 | 0(N) | 0(N) | 15(25) | 0/0 | NC | 0 |
| 22 | 78 | 0 | 47 | 0(N) | 0(N) | 10(5) | 0/0 | | 0 |
| 23 | 83m | 0 | 99 | 0(N) | 0(N) | 10(5) | 0/0 | | 80 |
| 24 | 84 | 0 | 87 | 0(N) | 0(N) | 5(0) | 0/0 | | 0 |
| 25 | 0 | 0 | 0 | 0(N) | 0(N) | 0(0) | 0/0 | | 0 |
| 26 | 83m | 0 | 91 | 0(N) | 30(N) | 5(5) | 0/0 | | 0 |
| 27 | 78m | 0 | 49 | 0(N) | 0(N) | 5(5) | 0/0 | | 0 |
| 28 | 99 | 0 | 98 | 0(N) | 10(N) | 25(30) | 0/0 | | 73 |
| 29 | 0 | 0 | 0 | 0(N) | 0(N) | 0(0) | 0/0 | | 0 |
| 30 | 0 | 0 | 0 | 0(N) | 0(N) | 5(0) | 0/0 | | 0 |
| 31 | 0 | — | 0 | 0(N) | 0(N) | 0(0) | 0/0 | | 0 |
| 32 | 0 | — | 0 | 0(N) | 0(N) | 15(0) | | | 0 |
| 33 | 0 | — | 0 | 0(N) | 0(N) | 5(0) | | | 0 |
| 34 | 0 | — | 0 | 0(N) | 30(N) | 0(0) | | | 0 |
| 35 | 0 | — | 0 | 0(N) | 0(N) | 5(5) | | | 0 |
| 36 | 0 | — | 0 | 0(N) | 0(N) | 0(0) | | | 0 |
| 37 | 0 | — | 0 | 0(N) | 0(N) | 0(0) | | | 0 |
| 41 | 67 | — | 87 | 0(N) | 0(N) | 5(5) | | | 0 |
| 48 | 0 | — | 0 | 0(N) | 0(N) | 5(0) | | | 0 |

[1]TSM = two-spotted spider mite (*Tetranychus urticae*);
GPA = green peach aphid (*Myzus persicae*);
BB = Mexican bean beetle (*Epilachna varivestis*);
AW = Southern armyworm (*Prodenia aeridania*);
HF = house fly (*Musca domestica*);
Nema = northern root-knot nematode (*Meloidogyne hapla*);
Mosq = mosquito; sy = systemic; (F) = % feeding;
(Kd) = knockdown; N = normal feeding; ME/L = mite egg/larvae;
m = total of % kill and % moribund.

TABLE V

POSTEMERGENCE HERBICIDAL ACTIVITY (10 lbs/acre)[4]

| Example No. | Postemergence | |
|---|---|---|
| | Monocota[2] | Dicota[3] |
| 1 | 5 | 82 |
| 2 | 35 | 60 |
| 3 | 67 | 57 |
| 4 | 97 | 95 |
| 5 | 90 | 62 |
| 6 | 62 | 85 |
| 8 | 12 | 30 |
| 9 | 47 | 90 |
| 11 | 12 | 30 |
| 12 | 96 | 97 |
| 13 | 99 | 100 |
| 16 | 92 | 94 |
| 17 | 50 | 60 |
| 19 | 27 | 42 |
| 20 | 22 | 95 |
| 21 | 55 | 97 |
| 22 | 79 | 90 |
| 23 | 72 | 97 |
| 24 | 85 | 77 |
| 25 | 30 | 82 |
| 26 | 90 | 82 |
| 27 | 75 | 80 |
| 29 | 35 | 75 |
| 30 | 70 | 97 |
| 34 | 10 | 72 |
| 35 | 12 | 72 |
| 37 | 12 | 50 |
| 38 | 10 | 57 |
| 41 | 30 | 77 |
| 52 | 37 | 45 |

[2]Monocot species tested: barnyard grass (*Echinochloa crusgalli*); crabgrass (*Digitaria* spp.); nutsedge (*Cyperus esculentus*); wild oats (*Avena fatus*).
[3]dicot species tested: bindweed (*Convolvulus arvensia*); curly dock (*Rumex crispus*); velvetleaf (*Abutilon theophrasti*); wild mustard (*Brassica haber*).
[4]no preemergence activity was found.

The metal complexes of the invention are also useful in seed treatment applications. By seed treatment is meant the disseminating of a biocidally active material over a seed subject to the attack of microorganism, and particularly fungi, in an amount which is effective to control such microorganisms without deleteriously effecting the seed. In most circumstances, the biocidally active material, in this case, the isothiazolone metal salt complexes will be applied to the surface area of the seeds to be treated. This can be accomplished by any convenient means well known in the art, such as slurrying, soaking, dusting, spraying and the like.

The amount of the isothiazolone complex required in an effective seed treatment application will vary depending upon conditions, such as the type of seed, the method of application, soil and atmospheric conditions and the like. Generally, an application in the range of about 0.25 to 20 ounces of isothiazolone complex per 100 pounds of seed will be effective to control any undesirable microorganisms and protect the seed. An application of the complex in the range of about 1.0 to 10 ounces per 100 pounds of seed is preferred.

Generally, control of a living organism is achieved in accordance with this invention by contacting the organism with an isothiazolone complex in an amount which is effective to control said organism. Any of the techniques known in the art can be employed to disseminate the complex to achieve the desired contact with the organism to be controlled. Spraying and fumigating are typical of such techniques.

The isothiazolone complexes of the invention can be readily utilized as slimicides, algaecides, bactericides, and fungicides in any locus and particularly in aqueous media, such as, for example, water-cooling systems, swimming pools, paper pulp processes, aqueous polymer dispersions, water-based paints, and the like. In addition, these complexes and compositions containing them are useful as, for example, fabric and leather preservatives, cosmetic preservatives, soap additives, sanitizing agents, such as in laundry soaps and detergents, and preservatives for metal working compounds, such as emulsifiable cutting oils, preservatives for fuels, fiber spin finish biocides, and the like.

In general, a locus subject to contamination by microorganisms can be protected in accordance with this invention by incorporating into the locus an isothiazolone complex in an amount which is effective to control the microorganisms. The term "contamination" is meant to include any attack by microorganisms which leads to a chemical or physical breakdown or disintegration of the locus as well as the proliferation of the microorganisms within the locus without an accompanying deleterious effect. The exact amount of isothiazolone complex required will, of course, vary with the medium being protected, the microorganisms being controlled, the particular complex or composition containing the complex which is employed and other factors. Typically, in a liquid medium, excellent control is obtained when the isothiazolone complexes are incorporated in the range of 0.1 to 10,000 parts per million (ppm) or 0.00001 to 1% based on the weight of the medium. A range of 1 to 2000 ppm is preferred.

The term "control," as employed in the specification and claims of this application includes any adverse affect on the existence or growth of a living organism or microorganism, such as complete killing action, eradication, arresting in growth, inhibition, reduction in number, or any combination of these effects.

Outstanding fungistatic activity is exhibited by the isothiazolone complexes of the invention when they are employed as paint preservatives and paint fungistats. Microbial activity in water-based and oil-based paint emulsions is effectively inhibited when the complexes are incorporated into the paint. The complexes are also highly active mildewcides for paint films when incorporated in paint formulations.

The isothiazolone complexes of the invention are also useful as agricultural fungicides. As such, they can conveniently be formulated in a fungicidal composition. Such compositions normally comprise an agronomically acceptable carrier and an isothiazolone complex or mixture of complexes as the active agent. Where necessary or desirable, surfactants or other additives may be incorporated to give uniformly formulated mixtures. By "agronomically acceptable carrier" is meant any substance which can be utilized to dissolve, dispense or diffuse the chemical incorporated therein without impairing the effectiveness of the toxic agent and which does no permanent damage to such environment as soil, equipment and agronomic crops.

For use as pesticides, the isothiazolone complexes of the invention are usually taken up in an agronomically acceptable carrier or formulated so as to render them suitable for subsequent dissemination. For example, the isothiazolone complexes can be formulated as wettable powders, emulsion concentrates, dusts, granular formulations, aerosols or flowable emulsifiable concentrates. In such formulations, the complexes are extended with a liquid or solid carrier and, when desired, suitable surfactants can be incorporated.

The complexes of the invention can be dissolved in a water-miscible liquid, such as ethanol, isopropanol, acetone, and the like. Such solutions are easily extended with water.

The isothiazolone complexes can be taken up on or mixed with a finely particled solid carrier, as for example, clays, inorganic silicates, carbonates, and silicas. Organic carriers can also be employed. Dust concentrates are commonly made wherein the isothiazolone complexes are present in the range of 20 to 80%. For ultimate applications, these concentrates are normally extended with additional solid from about 1 to 20%.

Wettable powder formulations are made by incorporating the complexes of this invention in an inert, finely divided solid carrier along with a surfactant which may be one or more emulsifying, wetting, dispersing or spreading agents or blend of these. The isothiazolone complexes are usually present in the range of 10 to 80% by weight and the surfactants in from 0.5 to 10% by weight. Commonly used emulsifying and wetting agents include polyoyethylated derivatives of alkylphenols, fatty alcohols, fatty acids, and alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the isothiazolone complex toxicant onto the solid carrier by means of a volatile solvent, such as acetone. In this manner adjuvants, such as activators, adhesives, plant nutrients, synergists and various surfactants, can also be incorporated.

Emulsifiable concentrate formulations can be prepared by dissolving the isothiazolone complexes of the invention in an agronomically acceptable organic solvent and adding a solvent-soluble emulsifying agent. Suitable solvents are usually water-immisciable and may be found in the hydrocarbon, chlorinated hydrocarbon, ketone, ester, alcohol and amide classes of organic solvents. Mixtures of solvents are commonly employed. The surfactants useful as emulsifying agents may constitute about 0.5 to 10% by weight of the emulsifiable concentrate and can be anionic, cationic or nonionic in character. Anionic surfactants include alcohol sulfates or sulfonates, alkylarene sulfonates and sulfosuccinates. Cationic surfactants include fatty acid alkylamine salts and fatty acid alkyl quaternaries. Nonionic emulsifying agents include alkylene oxide adducts of alkylphenols, fatty alcohols, mercaptans and fatty acids. The concentration of the active ingredients may vary from 10 to 80%, preferably in the range of 25 to 50%.

For use asphytopathogenic agents, the isothiazolone complexes are applied in an amount sufficient to exert the desired herbicidal activity. Usually, this will involve the application of the isothiazolone complexes to the locus to be protected by techniques well known in the art in an effective amount when incorporated in an agronomically acceptable carrier. However, it may be advantageous to apply the compounds directly onto the locus to be protected without the benefit of any substantial amount of carrier. This is a particularly effective method when the physical nature of the isothiazolone complex permits "low-volume" application, such as when the compounds are in liquid form or substantially soluble in higher boiling solvents.

The application rate will, of course, vary depending upon the purpose for such application, the complex being utilized, the frequency of dissemination and the like.

For use as agricultural bactericides, fungicides, nematocides, and insecticides, dilute sprays can be applied at concentrations of 0.05 to 20 pounds of the active isothiazolone complex per 100 gallons of spray. They are usually applied at 0.1 to 10 pounds per 100 gallons and preferably at 0.125 to 5 pounds per 100 gallons. In more concentrated sprays, the active ingredient is increased by a factor of 2 to 12. With dilute sprays, applications are usually made to the plants until run-off is achieved, whereas with more concentrated or low-volume sprays the materials are applied as mists.

The complexes of the invention may be utilized as the sole biocidal agents or they may be employed in conjunction with other fungicides, bactericides, algaecides, slimicides, insecticides, miticides, herbicides or with other comparable pesticides.

EXAMPLE A

Preservatives for Cutting Oils

Both natural and synthetic cutting oils, that is, oils which are mixed with water and used as coolants and lubricants in, for example, lathe and other metal-working operations, are extremely susceptible to microbial attack when formulated for use. This microbial attack leads to the production of odor and to the eventual breakdown of the oil formulation. The isothiazolone complexes of the invention are extremely useful in controlling microbial build-up, thus preventing this deleterious microbial attack, when incorporated in an emulsion or other diluted use formulation, either before or after the emulsification, at a level of about 0.1 to 10,000 parts per million of the use formulation. The preferred range of incorporation is about 10 to about 1000 parts per million in the final emulsion.

In order to evaluate the metal salt complexes as preservatives, samples of contaminated cutting oil from actual use operations were obtained. These contaminated samples were used to inoculate uncontaminated cutting oil formulations to which a metal salt complex had been added. After one month, the formulation was examined to determine whether the metal salt complex was effective in controlling microbial attack.

The metal salt complexes of Examples 4, 6, 10, 13, and 14 were tested. The contaminated samples containing them at levels of 10, 25, 50, 100, 250, and 500 ppm were found to have bacterial counts of less than 1000 cells/ml after one month. An untreated control had a bacterial count of greater than 10 million cells/ml after one month.

The data from these tests indicates the effectiveness of the metal salt complexes of the invention as preservatives in cutting oil formulations.

EXAMPLE B

Control of Algae, Bacteria, Fungi, and Slime in Cooling Towers

A constantly recurring problem in water-cooling systems is the out-of-control growth of algae, bacteria, and fungi, and the associated formation of slime. The isothiazolone complexes of the invention are quite effective in controlling algae, bacteria, fungi, and slime formation in water-cooling systems, and especially in water-cooling towers. When used as a cooling tower microbicide, the isothiazolone complex will generally be added at a concentration of about ½ to 1000 parts per million. The preferred concentration range of the complex is about 1 to 250 parts per million.

In an 8-week laboratory cooling tower test, the metal salt complex of Example 14 was found to keep the recirculating water clear and the cooling surfaces, reservoir walls, and tubing free of algae and non-algal slime. In a control which contained no biocide, the towers were completely fouled, with all surfaces covered with heavy deposits of algae and non-algal slime. This test demonstrates the effectiveness of metal salt complexes of the invention as water-cooling system biocides.

EXAMPLE C

Paint Film Mildewcides

Paint films from water-based and oil-based paints are quite susceptible to mildewing, especially when applied on exterior surfaces. Presently, various mercury compounds are generally used as paint mildewcides. However, these mercury compounds have several disadvantages, including their susceptibility to sulfide staining and their toxicity. The isothiazolone complexes of the invention are quite effective as paint mildewcides without the disadvantages of the mercurial mildewcides, and often with better performance than the mercury compounds. The concentration of isothiazolone complex which is added to the paint can vary over a wide range depending on such factors as the type of paint involved, the locality of application, and the type of surface on which the paint is applied. Generally, about 1/10 lb. to 20 lb. of the complex per 100 gallons of paint will be effective. The preferred range of incorporation is about ½ lb. to 12 lb. of the complex per 100 gallons of paint.

In order to evaluate isothiazolone complexes as mildewcides, wood sticks were painted with water-based paint formulations to which the complex being tested had been added. The paint films were allowed to dry for two days, treated with a test fungus (*Aspergillus niger* or *Pullularia pullulans*) and after 7 to 10 days were examined for evidence of mildew formation. The results of these tests are summarized in Table VI, which lists the isothiazolones tested and the minimum concentration (in pounds of isothiazolone per 100 gallons of paint) of isothiazolone which inhibits the growth of the fungus.

EXAMPLE C

TABLE VI

EFFECTIVENESS OF ISOTHIAZOLONE METAL SALT COMPLEXES AS PAINT-FILM MILDEWCIDES

| | Mildew Growth on Painted Wood Test Organism | | | | | | |
|---|---|---|---|---|---|---|---|
| | A. niger | | | P. pullulans | | | |
| Compound of | Pounds of Compound/100 Gal. Paint | | | | | | |
| Example No. | 0 | 0.5 | 1.0 | 2.0 | 0 | 0.5 | 1.0 | 2.0 |
| Control | 4+ | — | — | — | 4+ | — | — | — |
| 20 | — | + | + | 0 | — | 0 | 0 | 0 |
| 21 | — | 2+ | 0 | 0 | — | 0 | 0 | 0 |
| 23 | — | 4+ | 3+ | 0 | — | 0 | 0 | 0 |
| 24 | — | 3+ | 3+ | 1+ | — | 0 | 0 | 0 |
| 25 | — | 4+ | 4+ | 4+ | — | 1+ | 0 | 0 |
| 26 | — | 2+ | 2+ | 0 | — | 0 | 0 | 0 |
| 27 | — | 3+ | 1+ | 0 | — | 0 | 0 | 0 |

[1]Mildew growth evaluated on a scale of 0 to 4+, where 0 = no mildew growth and 4+ = heavy mildew growth.

The above data demonstrates the usefulness of the metal salt complexes of the invention as paint film mildewcides.

EXAMPLE D

Preservatives for Vinyl or Acrylic Emulsion Polymer Dispersions

On storage, aqueous dispersions of vinyl or acrylic emulsion polymers, such as those used in making water-based paints, may be subject to a buildup of microorganisms which may lead to the production of odor or discloration in the dispersion or to actual physical or chemical breakdown of the polymer.

Examples of such polymer dispersions include polyvinyl acetate; polyisobutylene; polystyrene; polymers of dienes, such as of isoprene, chloroprene, butadiene, including copolymers of butadiene with styrene, acrylonitrile or mixtures thereof; copolymers of (a) a soft acrylate, such as ($C_1$–$C_8$)alkyl acrylate (especially methyl acrylate, ethyl acrylate, butyl acrylate, 2-ethylhexyl acrylate or mixtures thereof), with (b) at least one hard comonomer, such as methyl methacrylate, acrylonitrile, styrene, vinyltoluene, vinyl acetate, and vinyl chloride, and (c) about 0.5 to 8% by weight of an $\alpha,\beta$-monoethylenically unsaturated acid, such as acrylic, methacrylic, crotonic, or itaconic acid such as those described in Conn. et al. U.S. Pat. No. 2,795,564, granted June 11, 1957; and blends of any of these polymer dispersions with each other or with similar polymers containing a polar group, such as any of the blends mentioned in Scott U.S. Pat. No. 3,356,627, granted Dec. 5, 1967.

The isothiazolone complexes of the invention are extremely effective in controlling buildup of microorganisms in such aqueous polymer dispersions and in water-base paints made from them thus preventing deleterious contamination of the dispersion or paint. An advantage of using the isothiazolone complexes as preservatives is that in proper concentration they will also function as mildewcides after the polymer dispersion or paint has been used to make a coating or film. When employed as preservatives, the isothiazolone complexes are usually incorporated in the polymer dispersion in a concentration range of about ½ to 10,000 parts per million. The preferred concentration range is about 1 to 2000 parts per million.

EXAMPLE E

PRESERVATIVES FOR COSMETICS

Emulsions of oil and water form cosmetics, including ointments and lotions. Inadvertently, these preparations become contaminated with microorganisms during manufacturing and by consumer use. Depending on the type of contaminants, these organisms may cause disease to the user or deleteriously affect the physical properties of the product.

The isothiazolone metal salt complexes of the invention were found to be effective preservatives at levels of 1–2000 ppm, preferably 10–500 ppm when incorporated in a variety of standard cosmetic formulations, including:

(1) Water/oil base formulation, consisting of 54% petrolatum, 6% sorbitan sesquiolate, and 40% water (2) Oil/water base formulation, consisting of 20% cetyl alcohol, 20% mineral oil, 0.5% sorbitan monooleate, 4.5% polyoxyethylene sorbitan monooleate and 55% water (3) Oil/water lotion formulation; consisting of 24.5% mineral oil, 1.5% sorbitan monosterate and 65.5% water.

Preservative tests are made by adding the isothiazolone compound to the cosmetic formulation and inoculating it with a mixture of the following nine pure bacterial and fungal cultures:

Pseudomonas oleoverans
Escherichia coli
Staphylococcus aureus
Serratia sp.
Aspergillus sp.
Penicillium sp.
Streptomyces sp.
Saccharomyces cerevisae
Cladosporium resinae The presence of viable microorganisms is determined after one month of incubation following inoculation. Table VII summarizes the results of these tests.

TABLE VII

EFFECTIVENESS OF METAL SALT COMPLEXES AS COSMETIC PRESERVATIVES

| Compound of Example No. | Cosmetic Formula No. 2 Level (ppm) | | | | | Cosmetic Formula No. 3 Level (ppm) | | | | |
|---|---|---|---|---|---|---|---|---|---|---|
| | 100 | 50 | 25 | 10 | 0 | 100 | 50 | 25 | 10 | 0 |
| 14 | Neg.* | Neg. | Neg. | Neg. | — | Neg. | Neg. | Neg. | Neg. | — |
| 10 | Neg.* | Neg. | Neg. | Neg. | — | Neg. | Neg. | Neg. | Neg. | — |
| 15 | Neg.* | Neg. | Neg. | Neg. | — | Neg. | Neg. | Neg. | Neg. | — |
| 13 | Neg.* | Neg. | Neg. | Neg. | — | Neg. | Neg. | Neg. | Neg. | — |
| 4 | Neg.* | Neg. | Neg. | Neg. | — | Neg. | Neg. | Neg. | Neg. | — |
| 9 | Neg.* | Neg. | Neg. | Neg. | — | Neg. | Neg. | Neg. | Neg. | — |
| Control | — | — | — | — | Pos. | — | — | — | — | Pos. |

*Presence of viable microorganism after 8 weeks incubation following inoculation.
Mixed Inoc.;
Ps. oleoverans, E. coli, S. aureus, Serratia sp., Asnergillus sp., Penicillium sp., Streptomyces sp., Saccharomyces cerevisae, Cladosporium resinae

EXAMPLE F

PAPER MILL SLIMICIDES

Slimicides are used in paper mills to control growth of micro-organisms in stored water suspensions of groundwood pulp and on equipment in contact with these suspensions or related water extracts. The microbial growths can cause severe physical and economical problems in a paper mill.

The metal salt complexes of the invention are effective microbicides and can be used to prevent slime in paper mills at concentrations of 0.5–1000 ppm, preferably 1–100 ppm, based on weight of compound per volume of white water.

Effectiveness of the metal salt complexes in this application may be evaluated in the laboratory by the following test. The slimicide is added to an artificial white water medium containing 0.1% groundwood pulp, 0.1% soluble starch, 0.1% HT clay and 0.3% $KH_2PO_4$. The medium is agitated in a flask, with one end of a tongue depressor stick immersed in the white water medium and the other end held firmly by a plastic foam stopper in the neck of the flask. The flasks are inoculated at zero time, and again after 7 and 14 days incubation, with a mixture of pure bacterial and fungal cultures consisting of *Pseudomonas fluorescens, Pseudomonas aeruginosa, Aerobacter aerogenes, Bacillus cereus* var. *mycoides, Flavobacterium suaveolans, Alcaligenes faecalis, Pullularia pullulans,* and *Aspergillus niger*. Samples of white water and stick accretion are evaluated for numbers of bacteria and fungi, once per week for 3 weeks (i.e., 7 days after each inoculation).

Table VIII summarizes the results of these tests.

TABLE VIII
PAPER MILL SLIMICIDE APPLICATION OF THE CALCIUM CHLORIDE COMPLEX OF 5-CHLORO-2-METHYL-4-ISOTHIAZOLIN-3-ONE (COMPOUND OF EXAMPLE NO. 14)

| Treatment Conc., ppm | Microflora Counted | % Reduction of Microorganisms at End of Three-Week Test* | |
|---|---|---|---|
| | | In White Water | On Stick Surface |
| 2.5 | Bacteria | >99.99 | >99.999 |
| | Fungi | 98.4 | 54.1 |
| 5 | Bacteria | >99.99 | >99.999 |
| | Fungi | >99.9 | 99.9 |
| 10 | Bacteria | >99.99 | >99.999 |
| | Fungi | 100 | >99.99 |

*Compared to untreated control:
Bacterial counts in control white water and on stick were 7.5 million/ml and 1.3 billion/stick, respectively; Fungal counts were 53,000/ml and 7.4 million per stick, respectively.

EXAMPLE G

JET FUEL PRESERVATIVES

Small quantities of water in jet fuel can encourage the growth of various hydrocarbon utilizing microorganisms. The resulting slime, and other particulate matter can cause fouling problems and equipment failure. The metal complexes of the invention can be used as preservatives to prevent growth of microorganisms in jet fuel when added at levels of 0.1 ppm to 1000 ppm, preferably 0.5-100 ppm.

Efficacy is determined by adding the test compound to a medium containing 9 parts JP5 Kerosene (jet fuel) and 1 part aqueous mineral salts medium, inoculating the medium with suitable microorganisms, and then evaluating for the presence of viable organisms in the medium after a sufficient incubation period to allow for growth of the microorganisms.

Table IX summarizes the results of these tests.

TABLE IX
JET FUEL PRESERVATIVES

| Conc. of PPM Compound** in Jet Fuel/Aqueous Mineral Salts Medium (ppm) | Microorganisms Present After 14 Days Incubation* |
|---|---|
| 0 | + |
| 1 | − |
| 5 | − |
| 10 | − |

*+ = present, − = absent
**Complex of Example 14

The isothiazolone complexes of the invention are also useful as microbicides in fiber spin finish formulation, such as nylon spin finish formulations and as laundry sanitizers.

It is to be understood that changes and variations may be made without departing from the spirit and scope of the invention as defined by the appended claims.

We claim:

1. A metal salt complex of the formula

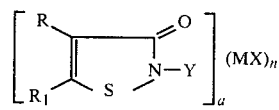

wherein
Y is a substituted alkyl group of 1-18 carbon atoms selected from hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, carbamoxyalkyl, isothiazolonyalkyl and cycloalkylaminoalkyl, an unsubstituted or substituted aryl group of up to 10 carbon atoms wherein the substituent is selected from halogen, cyano, nitro, ($C_1$-$C_4$) alkyl, ($C_1$-$C_4$) alkoxy, ($C_1$-$C_4$) alkylacylamino, ($C_1$-$C_4$) carbalkoxy, and sulfamyl, an unsubstituted or halo-substituted alkenyl, alkynyl group having 2-18 carbon atoms, unsubstituted or substituted cycloalkyl having 3-12 carbon atoms and in which the substituent is selected from halogen and methyl, an unsubstituted or substituted aralkyl having up to 10 carbon atoms, in which the substituent is selected from halogen, nitro, ($C_1$-$C_4$) alkyl, and ($C_1$-$C_4$) alkoxy;
R is hydrogen, halogen or a ($C_1$-$C_4$) alkyl group;
$R^1$ is hydrogen, halogen, or a ($C_1$-$C_4$) alkyl group; or R and R' can be taken together to complete a benzene ring, optionally substituted with one or more halogen atoms, nitro groups, ($C_1$-$C_4$) alkyl groups, cyano groups, or ($C_1$-$C_4$) alkoxy groups;
M is a cation of barium, cadmium, calcium, chromium, cobalt, copper, iron, lead, lithium, magnesium, manganese, mercury, nickel, silver, sodium, strontium, tin, or zinc;
X is a chloride, bromide, iodide, sulfate, nitrate, acetate, perchlorate, bisulfate, bicarbonate, oxalate, maleate, p-toluenesulfonate, carbonate, or phosphate anion;
a is the integer 1 or 2; and
n is the integer for which the anion X satisfies the valence of the cation M.

2. A complex according to claim 1 wherein R and R' are hydrogen.

3. A complex according to claim 1 wherein R is hydrogen and R' is halogen.

4. A complex according to claim 1 wherein Y is an unsubstituted or substituted aralkyl group of up to 10 carbon atoms.

5. A complex according to claim 1 wherein Y is an unsubstituted or substituted aryl group of up to 10 carbon atoms.

6. The composition of claim 1 in which at least one of R' and R is chloro, and wherein Y is a substituted alkyl group having up to 10 carbon atoms and the substituents are selected from halogen, nitro, ($C_1$-$C_4$) alkyl, and ($C_1$-$C_4$) alkoxy.

7. The composition of claim 6 in which $R^1$ is chloro and R is hydrogen or ($C_1$-$C_4$) alkyl.

8. The composition of claim 7 in which M is zinc, copper, nickel, manganese, calcium, magnesium, mercury, cadmium, cobalt, or chromium and in which the anion X is chloride.

9. The complex of claim 8 in which M is calcium, copper, magnesium, manganese, nickel, or zinc.

10. A complex according to claim 9 wherein X is a chloride anion.

* * * * *